(12) United States Patent
Geisen et al.

(10) Patent No.: US 6,497,009 B2
(45) Date of Patent: Dec. 24, 2002

(54) APPARATUS FOR PROVIDING A FLOCK-AIR MIXTURE SUBSTANTIALLY FREE FROM FLOCK LUMPS AND A METHOD OF DISPERSING FLOCK LUMPS

(75) Inventors: Armin Geisen, Melsbach (DE); Ulrich Mertgen, Meinborn (DE); Sascha Haase, Neuwied (DE)

(73) Assignee: Winkler & Dunnebier Aktiengesellschaft, Neuwied (DE)

( * ) Notice: Subject to any disclaimer, the term of this patent is extended or adjusted under 35 U.S.C. 154(b) by 0 days.

(21) Appl. No.: 09/851,785

(22) Filed: May 9, 2001

(65) Prior Publication Data

US 2002/0002760 A1 Jan. 10, 2002

(30) Foreign Application Priority Data

May 9, 2000 (DE) .......................... 100 22 499

(51) Int. Cl.⁷ .............................................. D01G 25/00
(52) U.S. Cl. ........................................... 19/296; 19/308
(58) Field of Search ....................... 19/105, 145, 145.5, 19/145.7, 145.3, 144, 296, 300–308; 156/62.2, 322, 499, 296; 162/251; 209/17, 135, 138, 139.1; 264/112, 121, 518; 403/292, 294, 401; 406/12, 98, 106, 168; 492/32, 37, 38; 425/80.1, 81.1

(56) References Cited

U.S. PATENT DOCUMENTS

| | | | | |
|---|---|---|---|---|
| 1,834,309 A | | 12/1931 | Harney | |
| 2,646,381 A | * | 7/1953 | Duvall | 264/121 |
| 2,940,133 A | | 6/1960 | Heritage | 19/156 |
| 2,940,134 A | | 6/1960 | Heritage | 19/156 |
| 2,940,135 A | | 6/1960 | Heritage | 19/156 |
| 3,037,248 A | * | 6/1962 | Callaghan | 19/308 |
| 3,616,035 A | * | 10/1971 | Baskerville, Jr. et al. | 156/296 |
| 3,797,074 A | * | 3/1974 | Zafiroglu | 19/306 |
| 3,862,472 A | * | 1/1975 | Norton et al. | 19/145.5 |
| 3,886,629 A | | 6/1975 | Nakai et al. | 19/156.3 |
| 4,153,978 A | | 5/1979 | Bangert | 19/304 |
| 4,375,447 A | | 3/1983 | Chung | 264/518 |
| 4,383,349 A | | 5/1983 | Marshall | 19/0.56 |
| 4,712,277 A | * | 12/1987 | Gustavsson | 19/296 |
| 5,044,052 A | | 9/1991 | Hertel et al. | 28/105 |
| 6,297,201 B1 | * | 8/2001 | Jonasson et al. | 19/308 |

FOREIGN PATENT DOCUMENTS

| | | |
|---|---|---|
| DE | 1 510 395 | 3/1972 |
| DE | 26 29 901 | 2/1977 |
| DE | 4006 180 A1 | 9/1990 |
| DE | 43 19 445 A1 | 12/1994 |
| DE | 197 06 404 A1 | 8/1998 |
| EP | 0 515 939 A1 | 12/1992 |

OTHER PUBLICATIONS

Patent Abstracts of Japan, Publication No. 62231032, Publication Date Oct. 9, 1987, 1 page.
European Patent Office Search Report dated Aug. 17, 2001, 4 pages.

* cited by examiner

Primary Examiner—Gary L. Welch
(74) Attorney, Agent, or Firm—Rosenthal & Osha L.L.P.

(57) ABSTRACT

In an apparatus and a process for preparing a flock-air mixture which is fed by a pulping device through a feed conduit to a flock-laying device for forming an absorbent pad, the feed conduit includes a dispersing device for loosening up lumps of flock within the mixture. To achieve a high level of efficiency in loosening the flock lumps, as independently as possible of the through-put of the mixture through the feed conduit, the dispersing device is in the form of a pneumatic dispersing device which loosens up the lumps by accelerating the mixture with lumps therein to cause the lumps to burst or tear apart.

14 Claims, 4 Drawing Sheets

APPARATUS FOR PROVIDING A FLOCK-AIR MIXTURE SUBSTANTIALLY FREE FROM FLOCK LUMPS AND A METHOD OF DISPERSING FLOCK LUMPS

FIELD OF THE INVENTION

The present invention concerns an apparatus for preparing a flock-air mixture intended for example for forming an absorbent pad and a method of dispersing lumps in a flock-air mixture.

BACKGROUND OF THE INVENTION

In the case of machines for producing absorbent pads as for sanitary napkins, panty liners, disposable diapers or the like, the usual practice is for an absorbent pad or flock core to be formed from a hydrophilic flock mixture on a flock-laying device. The flocks which are required for that purpose are fed to the flock-laying device in the form of a flock-air mixture, being supplied thereto from a disintegrating or pulping device, through a feed conduit.

For reasons relating to environmental protection and anti-noise measures, it has become the usual practice for the disintegrating device to be arranged spatially separately from the flock-laying device, with a blower or fan being integrated into the feed conduit in order to ensure that the flock-air mixture can suitably cover the conveying distance which has been increased as a result. Due to friction in the feed conduit, flow turbulence phenomena and a static charging effect, flock lumps or compacted pieces of flock are formed within the flock-air mixture as it flows through the greater length of the feed conduit. That contributes to preventing the desired homogeneous flock structure of the absorbent pad and in addition has an adverse effect on the mechanical stability of the absorbent pad as lumps are only laid into the flock mesh structure of the absorbent pad but are not properly bound thereinto.

An additional driven grinding rotor can be integrated into the feed conduit which carries the flock to the flock-laying device, in order to break up the flock lumps, near the flock-laying device. That technology is described for example in U.S. Pat. Nos. 1,834,309, 2,940,133, 2,940,134, 2,940,135, 3,886,629 and 4,375,447. A disadvantage with those known arrangements is that they are generally expensive and they also take up a considerable amount of space. The grinding rotors for disintegrating the flock lumps require a rotary drive, the speed of rotation of which has to be suitably adapted in dependence on the through-put rate of the flock-air mixture. In addition, the rotors give rise to unwanted air turbulence phenomena which act in opposition to the uniform formation of the absorbent pad.

As an alternative to the provision of a grinding rotor in the feed conduit which carries the flock-air mixture, EP 0 515 939 A1 provides for the incorporation of a mechanical impact device in the feed conduit. That impact device comprises a plurality of impact bars which project into the cross-section of the feed conduit for transporting the flock-air mixture. The flock lumps which are contained in the flock-air mixture and which, upon being transported from the disintegrating device to the flock-laying device, impact against the impact bars are very substantially broken up by virtue of that mechanical collision effect. It has been found however that this impact device suffers from the disadvantage that on the one hand considerable amounts of lumps of flock still do not collide with the impact bars and are therefore not broken up, while on the other hand the degree of efficiency in terms of flock lump dispersion depends on the through-put of the flock-air mixture through the feed conduit as it is the through-put speed of the mixture through the feed conduit that determines the speed at which the lumps of flock impact against the bars.

SUMMARY OF THE INVENTION

An object of the present invention is to provide an apparatus for preparing a flock-air mixture which is substantially free of flock lumps, which affords an enhanced level of efficiency in terms of dispersing the lumps.

Another object of the invention is to provide an apparatus for preparing a substantially lump-free flock-air mixture, with which the efficiency of lump dispersion is at least substantially independent of the speed of flow of the flock-air mixture through a feed conduit leading to a flock-processing device.

Still another object of the present invention is to provide a method of dispersing lumps of flock in a flowing flock-air mixture, such as to enhance the efficiency with which the lumps are dispersed without substantial dependence on the speed of flow of the flock-air mixture.

Yet another object of the present invention is to provide a method of dispersing flock lumps in a flock-air mixture, which affords a simple but reliable and effective operating procedure.

In accordance with the principles of the present invention, in regard to the apparatus, the foregoing and other objects are attained by an apparatus for providing a flock-air mixture which is to be fed through a feed conduit to a flock-laying device for forming an absorbent pad. Provided in the feed conduit is a dispersing device for dispersing flock lumps within the flock-air mixture. The dispersing device is a pneumatic dispersing device operable to loosen up and disperse flock lumps by accelerating the flock-air mixture together with the lumps contained therein to cause the lumps to be broken up, as by tearing the lumps apart or by causing them to burst asunder.

Further in accordance with the principles of the present invention, in regard to the method aspect, the foregoing and other objects are attained by a method of dispersing flock lumps within a flock-air mixture passing through a feed conduit to a flock-laying device for forming an absorbent pad, wherein, prior to formation of the absorbent pad in the flock-laying device, the flock-air mixture together with the flock lumps contained therein is accelerated by means of a pneumatic dispersing action thereby to cause the flock lumps to break up.

It was surprisingly found that flock lumps which comprise compacted cellulose flocks or fibers can be broken up and dispersed if they are accelerated suddenly with a jerk, jolt or jump by means of a directed flow of fluid, in particular an air flow, of high kinetic energy. In that situation, acceleration and/or fluid friction forces occur, which readily overcome the mechanical and/or electrostatic adhesion forces which are operative between the flocks forming a flock lump. Furthermore, the pneumatic dispersing device according to the invention preferably generates turbulent flows whose acceleration effects which change randomly in respect of direction and magnitude have the result that the flock lumps disintegrate.

Depending on the respective magnitude of the forces which hold a flock lump together, dispersion of the flock lump occurs at an earlier or later time. A flock lump which is less firmly held together can already be torn apart at the beginning of the acceleration phase whereas a flock lump which is more firmly held together can under some circumstances be destroyed only after the attainment of an adequate degree of turbulence in the flow of the flock-air mixture. At any event the apparatus and the method according to the invention provide that, in contrast to the impact arrangements discussed above, all flock lumps contained in the flock-air mixture flowing through the feed conduit are operatively engaged by the acceleration forces to cause appropriate disintegration and dispersion thereof.

In accordance with a preferred feature of the apparatus of the invention, the pneumatic dispersing device can be arranged in the end region of the feed conduit which carries the flow of the flock-air mixture. Preferably, the dispersing device is fitted directly into the opening of the feed conduit into the flock-laying device. The flock-laying device includes a rotating flock-shaping wheel and a stationary flock box into which the feed conduit opens by way of the pneumatic dispersing device. The directed jet of the substantially lump-free flock-air mixture which is produced by the pneumatic dispersing device means that it is advantageously possible for that jet to be directed specifically and targetedly in a given direction in space. This means that troughs or shaping recesses provided in the peripheral surface of the flock-shaping wheel, for forming the absorbent pads, can be more effectively filled with flock.

In accordance with another preferred feature of the invention the pneumatic dispersing device can be formed by a nozzle around which the flock-air mixture flows. The nozzle is arranged substantially in the central region of the cross-section of the feed conduit between the disintegrating device and the flock-laying device. With this configuration of the dispersing device it will be noted that it is necessary for the compressed air which is to be discharged from the nozzle under high pressure to be introduced into the central region of the cross-section of the feed conduit. The consequence of this is that at least one suitable pneumatic line must be passed into the central region of the cross-section of the feed conduit, which means that the at least one pneumatic line is in the flow path of the flock-air mixture and thus, in addition to the pneumatic action of dispersing the flock lumps, can also afford a mechanical dispersing action in the manner of the abovediscussed impact bars.

In a further preferred feature the pneumatic dispersing device is in the form of an injector nozzle in the form of a tube portion, with the flock-air mixture flowing through the injector nozzle itself. A pressure fluid under high pressure, more particularly for example compressed air, is fed to the injector nozzle by way of one and preferably a plurality of flow openings which are in the form of feed passages. The pressure fluid can either come from a pressure fluid source which is additionally provided for that purpose, or it can come from a pressure fluid source which in any case is already present for other systems of the machines involved in the present context. The preferably plurality of feed passages in accordance with the invention can be disposed in the outer peripheral region of the flow space of the injector nozzle, through which the flock-air mixture flows.

It will be appreciated that the pneumatic dispersing device or injector nozzle acts in a fluid-mechanics fashion like a fluid or air flow booster. A reduced pressure obtains at the entry or intake side while an increased pressure occurs at the exit or ejection side thereof. The dispersing device or injector nozzle can therefore act like a suction blower arranged at the end of the feed conduit which carries the flock-air mixture, so that, depending on the respective overall length of the feed conduit, it is possible to forego the inclusion of a further fan or blower in the flock-delivery path.

In regard to a preferred feature of the method of the invention, it has proven to be particularly advantageous for the flock-air mixture to be accelerated to a supersonic speed, preferably to twice the speed of sound. Such high speeds ensure that turbulent flows are produced in the dispersing device or injector nozzle and the flock-air mixture is accordingly sufficiently accelerated with a jerk, jolt or jump effect.

Further objects, features and advantages of the invention will be apparent from the description hereinafter of a preferred embodiment of the invention.

DESCRIPTION OF THE PREFERRED EMBODIMENT

Figure 1:
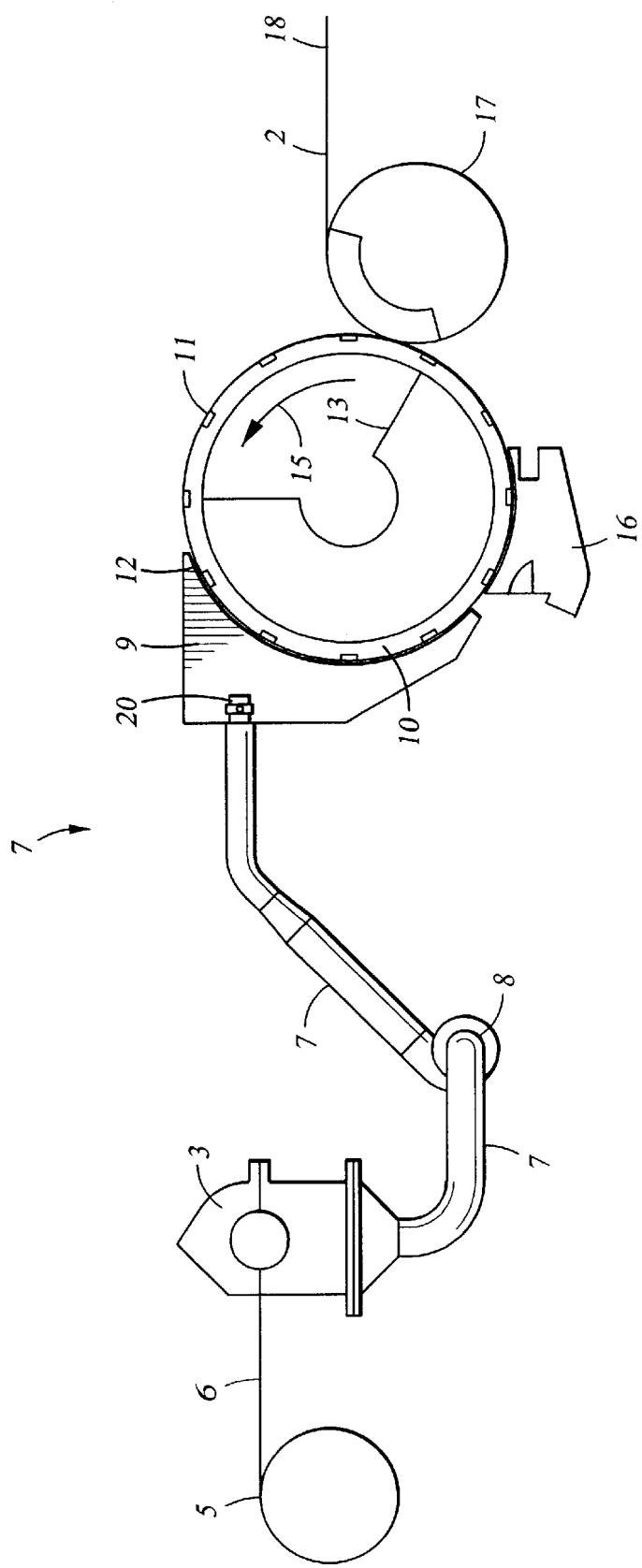
FIG. 1 is a diagrammatic side view of an apparatus according to the invention for providing a flock-air mixture for the production of absorbent pads.

Referring firstly to FIG. 1, shown therein is an apparatus according to the invention for providing a flock-air mixture which is substantially free from lumps and clumps of flock and which can then be used for producing flock cores or absorbent pads as indicated at 2 in FIG. 1 for sanitary napkins, panty liners, disposable diapers or similar hygiene articles. A crushing device or disintegrating device 3 is supplied from a supply roll 5 with a cardboard or cellulose web 6. The web 6 is broken up into cellulose flocks or pulp in the disintegrating device 3. Alternatively, the cellulose flocks could also be made available in some other fashion, for example they may already be available in the form of ready cellulose flocks. Those flocks are mixed with carrier air and are transported in the form of a flock-air mixture through a feed conduit 7 to a flock-laying device indicated generally by reference 4. Depending on the respective length of the feed conduit 7, the assembly may include a fan or blower 8 for supporting the flow of carrier air in the course of the feed conduit 7.

The flock-laying device 4 substantially includes a flock-shaping wheel 10 and a hollow flock box 9 which covers over the flock-shaping wheel 10 in a predetermined peripheral region thereof and is open there to the flock-shaping wheel 10. The flock-shaping wheel 10 rotates in the counter-clockwise direction as indicated by the arrow 15. In its peripheral casing or in its outer peripheral region the flock-shaping wheel 10 has troughs or shaping recesses 11 which are provided with sieve-like bottoms 12. A suction box 13 which is stationary, that is to say which does not therefore rotate with the flock-shaping wheel 10, makes it possible for flock-air mixture to be sucked into the shaping recesses 11 through the sieve-like bottoms 12, in that peripheral region of the flock-shaping wheel 10 which is covered over by the flock box 9. As a result, the desired flock cores or absorbent pads 2 are formed in those shaping recesses 11 which are in the region which is covered over by the flock box 9.

Arranged at an upstream position in relation to the flock-shaping wheel 10 in the direction of rotation as indicated by the arrow 15 is a brushing-off device 16 which removes the flock material projecting beyond the outer peripheral surface from the shaping recesses 11, and which feeds the removed flock material back to the disintegrating device 3 by way of a return conduit (not shown). Then, the absorbent pads which have been brushed flush with the peripheral surface of the wheel 10 in that way are removed from the shaping recesses 11 by means of a suction roller 17 and placed on a conveyor belt 18 which feeds them to a machine (not shown) for the production of sanitary napkins, panty liners, diapers or the like.

It will be apparent from FIG. 1 that the feed conduit 7 opens directly into the flock box 9. In this arrangement, the pneumatic dispersing device which in the illustrated structure is in the form of an injector nozzle as diagrammatically indicated at 20 is already disposed entirely within the flock box 9. In that way, the freedom of movement of the injector nozzle 20 is not limited by the flock box wall which delimits the flock box 9 towards the left in FIG. 1, so that the discharge direction of the jet of flock-air mixture which leaves the injector nozzle 20 can be set to be in a given specific direction in space without any problem. Alternatively however the injector nozzle 20 can also be arranged outside the flock box 9.

Figure 2:
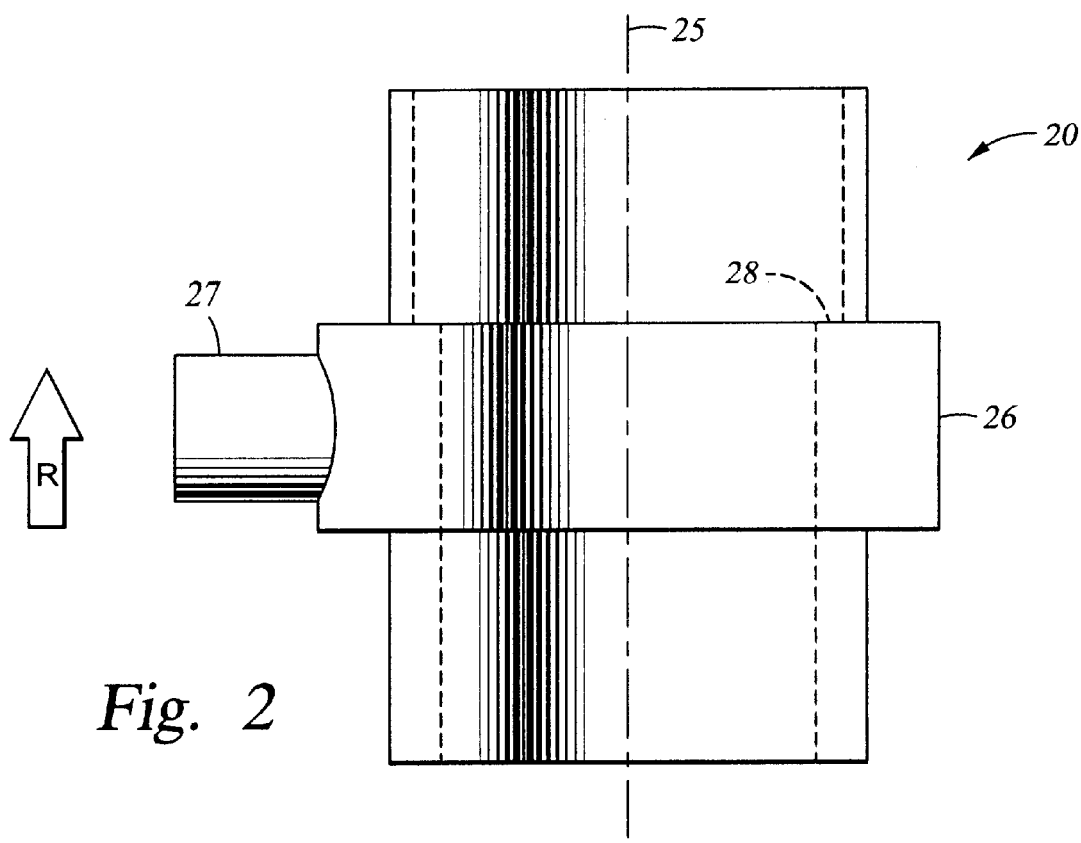
FIG. 2 is a diagrammatic view showing a pneumatic dispersing device in the form of an injector nozzle.
Figure 3:
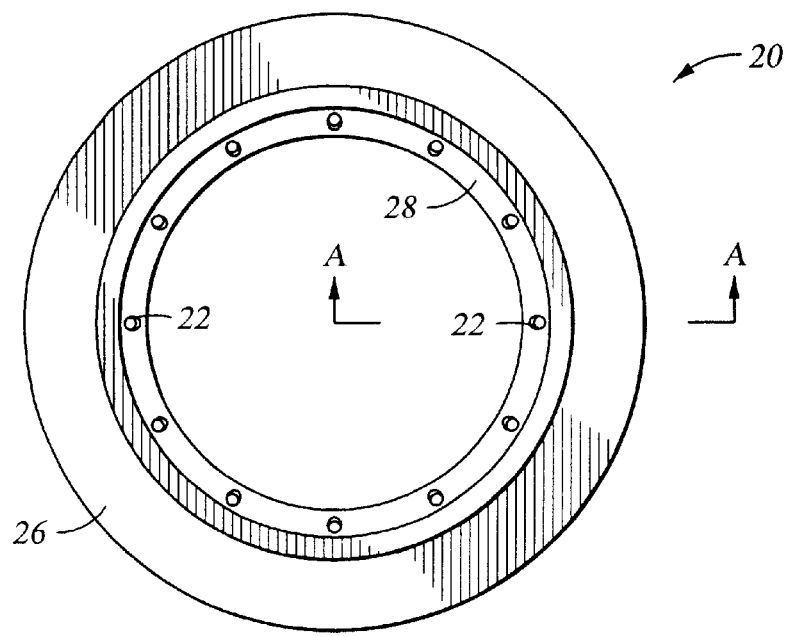
FIG. 3 is a view of the injector nozzle of FIG. 2 from above.

Reference will now be made to FIGS. 2 and 3 showing the injector nozzle 20 which operates as the pneumatic dispersing device. The injector nozzle 20 comprises a comparatively short tube portion which is fitted into the downstream end of the feed conduit indicated at 7 in FIG. 1. In its region which is the central region in its longitudinal direction, the injector nozzle 20 has a bead or ridge portion 26 in which there is provided an annular passage which extends entirely therearound and which is indicated at 23 in the sectional view illustrated in FIG. 4. The annular passage 23 is in flow communication by way of a connecting portion indicated at 27 in FIG. 2 with a pneumatic or compressed air source (not shown) which can be provided specifically for the injector nozzle 20 or which is already present for use with other systems of the respective machine.

In the view shown in FIG. 2, the flock-air mixture flows upwardly through the injector nozzle 20 as indicated by the arrow R. In doing so, it flows in particular through the flow space indicated at 21 in the interior of the injector nozzle 20, the flow space 21 being of a cylindrical cross-section in the illustrated embodiment. Alternatively however, it may also be of a cross-section which increases in the flow direction R and thereby act as a diffuser. As can be clearly seen from FIGS. 2 and 3 the flow space 21 is of a larger inside diameter than the remaining space, which is shown therebeneath in FIG. 2, in the interior of the injector nozzle 20. That design configuration affords a step 28 in the form of a circular ring at the level of the lower plane defining the flow space 21, as is shown in the plan view of FIG. 3.

Figure 4:
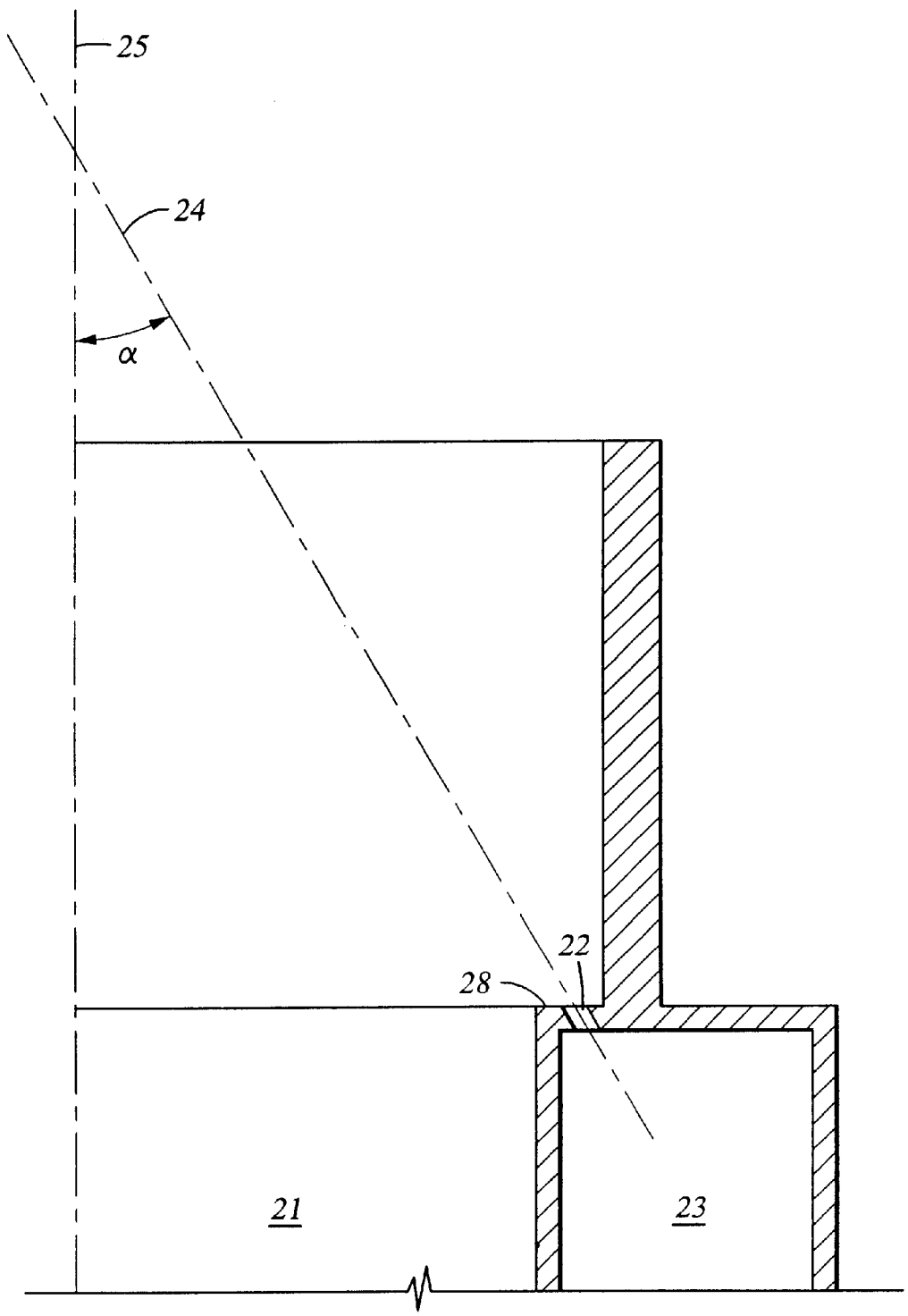
FIG. 4 is a view in section on line A—A in FIG. 3.
Figure 5A:
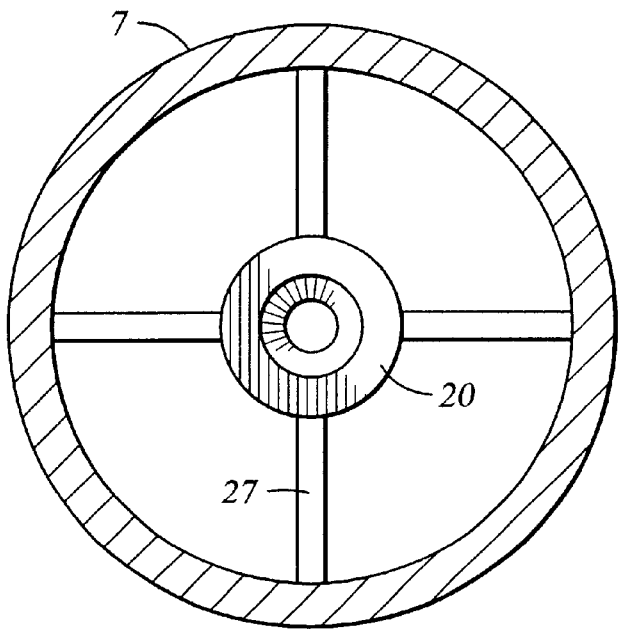
FIG. 5A is a cross-sectional view of the embodiment in the axial direction of the feed conduit.
Figure 5B:
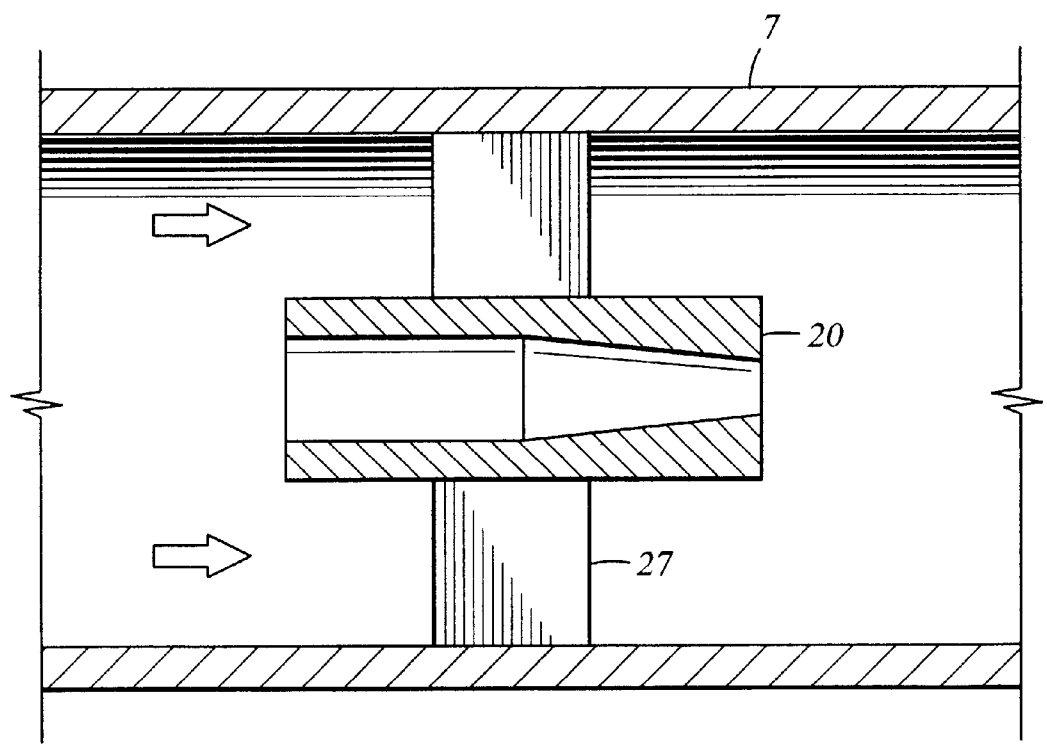
FIG. 5B is a longitudinal cross-sectional view of the embodiment.

As can best be seen from FIGS. 3 and 4, a total of twelve feed passages 22 which act as feed openings open into the annular surface of the step 28 in the illustrated embodiment. The feed passages 22 are distributed at uniform angular spacings over the peripheral extent of the step 28. Alternatively however it is also possible to provide more than or fewer than twelve feed passages, or to arrange the feed passages at nonuniform angular spacings in order if necessary to produce specific flow profiles over the cross-section of the injector nozzle 20.

As shown in FIG. 4, the feed passages 22 are in flow communication with the annular passage 23 and therefore also with the compressed air source which is connected to the connecting portion indicated at 27 in FIG. 2.

Looking still at FIG. 4, the axis as indicated at 24 of the feed passage 22 shown therein is inclined at the angle of inclination $\alpha$ with respect to the longitudinal axis or axis of symmetry as indicated at 25 of the injector nozzle 20. The longitudinal axis is also indicated at 25 in FIG. 2. That configuration provides that the compressed air is supplied not just axially in the flow direction indicated at R in FIG. 2, but also with a velocity component which is directed radially inwardly towards the longitudinal axis 25. That action, in addition to the acceleration forces which break up and disperse the flock lumps, can also produce a further effect which promotes dispersion of the flock lumps and which provides that the flock lumps present are blown radially inwardly out of the radially outer regions of the cross-section of the jet of flock-air mixture and are thereby caused under some circumstances to collide with each other whereby they are torn apart or broken up. In accordance with the invention the angle of inclination a can be 50° or less, with the inequality $5° \leqq \alpha \leqq 30°$ preferably applying. Alternatively the angle $\alpha$ can also be 0°, which therefore means that the axis 24 of the feed passages 22 extends parallel to the longitudinal axis 25 of the injector nozzle 20.

Instead of a plurality of feed openings 22 in the form of bored passages, it is also possible to provide a single feed opening in the form of a peripherally extending passage in the nature of an annular gap, between the annular passage 23 and the flow space 21. With that structure, a larger cross-sectional area is available to the compressed air to be supplied, for it to flow into the flow space 21, so that a larger and spatially better distributed volume flow of compressed air can be fed to the flow space 21 and it is in that way possible to achieve a higher degree of effectiveness in terms of dispersing the flock lumps in the flock-air mixture.

It will be appreciated that the above-described apparatus for producing a flock-air mixture which is substantially free from flock lumps and the concomitant method of dispersing flock lumps within the flock-air mixture as it is fed through a feed conduit have been set forth solely by way of example and illustration of the principles of the invention and that various other modifications and alterations may be made therein without thereby departing from the spirit and scope of the invention.

What is claimed is:

1. An apparatus for providing a flock-air mixture to be fed through a feed conduit to a flock-laying device for forming an absorbent pad, including in the feed conduit:

a dispersing device for dispersing flock lumps within the flock-air mixture, the dispersing device being a pneumatic dispersing device operable to loosen up flock lumps by accelerating the flock-air mixture together with the lumps contained therein to cause the lumps to be broken up, wherein the dispersing device includes:

a nozzle having at least one nozzle passage arranged substantially in a central region of a cross-section of the feed conduit and so positioned that the flock-air mixture in operation of the apparatus flows in a flow path therearound; and further including:

a pneumatic line for feeding pressure fluid from a pressure fluid source to the nozzle passage to accelerate the flock lumps, wherein the pneumatic line extends in said flow path thereby effecting additional mechanical dispersing action regarding the flock lumps.

2. Apparatus as set forth in claim 1 wherein the dispersing device is operable to tear flock lumps apart.

3. Apparatus as set forth in claim 1
wherein the dispersing device is operable to burst flock lumps.

4. Apparatus as set forth in claim 1
wherein the feed conduit has a downstream end region and the dispersing device is arranged in the downstream end region of the feed conduit.

5. An apparatus for providing a flock-air mixture to be fed through a feed conduit to a flock-laying device for forming an absorbent pad, including in the feed conduit:
  a dispersing device for dispersing flock lumps within the flock-air mixture, the dispersing device being a pneumatic dispersing device operable to break up flock lumps by accelerating the flock-air mixture together with the lumps contained therein to cause the lumps to be broken up, wherein the dispersing device includes:
  an injector nozzle in the form of a tube portion and having a flow space for the flow therethrough of the flock-air mixture, the flow space including an outer peripheral region and comprising:
    at least one feed opening in the outer peripheral region of the flow space for a feed therethrough to the flow space or pressure fluid for accelerating the flock lumps from a source of pressure fluid.

6. Apparatus as set forth in claim 5 and including
an annular passage in flow communication with the at least one feed opening for supply with the pressure fluid.

7. Apparatus as set forth in claim 6 and including
a plurality of feed openings in the form of feed passages at uniform angular spacings in the outer peripheral region of the flow space.

8. Apparatus as set forth in claim 5, wherein the injector nozzle has a longitudinal axis and an axis of the at least one feed opening extends in parallel relationship with the longitudinal axis of the injector nozzle, the arrangement being such that the pressure fluid is fed to the flow space substantially axially in the flow direction of the flock-air mixture.

9. Apparatus as set forth in claim 5, wherein the injector nozzle has a longitudinal axis and an axis of the at least one feed opening is inclined at an angle with respect to the longitudinal axis of the injector nozzle, the arrangement being such that the pressure fluid is fed to the flow space both with an axial and with a radial flow component.

10. Apparatus as set forth in claim 9, wherein an inequality $0 \leq \alpha \leq 50°$ applies for the angle of inclination.

11. Apparatus as set forth in claim 10
wherein the inequality $5 \leq \alpha \leq 30°$ applies for the angle of inclination.

12. A method of dispersing flock lumps within a flock-air mixture which is fed in a flow direction through a feed conduit to a flock-laying device for forming an absorbent pad, comprising:
  accelerating the flock-air mixture, in said flow direction, with the flock lumps contained therein, prior to formation of an absorbent pad in the flock-laying device, by means of a pneumatic dispersing action thereby to cause the flock lumps to be broken up,
  said accelerating being effected by an injector nozzle in the form of a tube portion having an entry side for entry of the flock-air mixture and an exit side for exit of the flock air mixture, wherein a pressurized fluid is fed in said flow direction through the nozzle thereby generating a reduced pressure at the entry side and an increased pressure at the exit side.

13. A method of dispersing flock lumps within a flock-air mixture which is fed in a flow direction through a feed conduit to a flock-laying device for forming an absorbent pad, comprising:
  accelerating the flock-air mixture, in said flow direction, with the flock lumps contained therein, prior to formation of an absorbent pad in the flock-laying device, by means of a pneumatic dispersing action thereby to cause the flock lumps to be broken up,
  said accelerating being effected by an injector nozzle in the form of a tube portion having an entry side for entry of the flock-air mixture and an exit side for exit of the flock air mixture, wherein a pressurized fluid is fed in said flow direction through the nozzle thereby generating a reduced pressure at the entry side and an increased pressure at the exit side,
  wherein the flock-air mixture is accelerated to supersonic speed.

14. A method as set forth in claim 13
wherein the flock-air mixture is accelerated to approximately twice the speed of sound.

* * * * *